United States Patent
Matsumoto et al.

[11] Patent Number: 6,136,763
[45] Date of Patent: Oct. 24, 2000

[54] SELECTIVE REMOVING METHOD OF SEBUM

[75] Inventors: Yasunobu Matsumoto; Tomoko Kondo, both of Tokyo, Japan

[73] Assignee: Kao Corporation, Tokyo, Japan

[21] Appl. No.: 09/255,859

[22] Filed: Feb. 23, 1999

[30] Foreign Application Priority Data

Feb. 24, 1998 [JP] Japan .................................. 10-041869
Aug. 31, 1998 [JP] Japan .................................. 10-245646

[51] Int. Cl.⁷ .............................. C11D 7/48; A61K 7/02
[52] U.S. Cl. ..................... 510/130; 510/136; 510/140; 510/406; 424/401; 424/402; 424/69; 424/70.1
[58] Field of Search ................. 510/136, 140, 510/406, 505; 424/401, 402, 69, 70.1

[56] References Cited

U.S. PATENT DOCUMENTS

| | | | |
|---|---|---|---|
| 3,795,624 | 3/1974 | Feinstone | 424/401 |
| 3,912,667 | 10/1975 | Spitzer et al. | 521/65 |
| 3,976,781 | 8/1976 | Kalopissis | 514/538 |
| 4,073,898 | 2/1978 | Bouillon et al. | 514/164 |
| 4,085,217 | 4/1978 | Kalopissis | 514/355 |
| 4,087,550 | 5/1978 | Bouillon et al. | 514/562 |
| 4,388,301 | 6/1983 | Klein | 424/684 |
| 4,529,587 | 7/1985 | Green | 424/70.8 |
| 4,540,507 | 9/1985 | Grollier | 424/70.19 |
| 4,715,982 | 12/1987 | Zabotto et al. | 510/131 |
| 4,778,675 | 10/1988 | Vanlerberghe et al. | 424/70.21 |
| 4,806,572 | 2/1989 | Kellett | 521/112 |
| 4,954,532 | 9/1990 | Elliot et al. | 514/63 |
| 5,011,681 | 4/1991 | Ciotti et al. | 510/136 |
| 5,217,641 | 6/1993 | Herstein | 510/136 |
| 5,441,667 | 8/1995 | Tonomura et al. | 379/67.1 |
| 5,462,691 | 10/1995 | Shimada et al. | 510/159 |
| 5,565,207 | 10/1996 | Kashibuchi et al. | 424/401 |
| 5,716,626 | 2/1998 | Sakurai et al. | 424/401 |
| 5,730,964 | 3/1998 | Waldstreicher | 424/65 |
| 5,741,766 | 4/1998 | Marion et al. | 510/130 |
| 5,773,015 | 6/1998 | Bajor et al. | 424/401 |
| 5,851,978 | 12/1998 | Shana'a | 510/417 |

OTHER PUBLICATIONS

Umbach, Wilfried. Cosmetics and Tioletries; Development, Production and Use. pp. 306–307, 1991.

Primary Examiner—Yogendra Gupta
Assistant Examiner—Christine Ingersoll
Attorney, Agent, or Firm—Oblon, Spivak, McClelland, Maier & Neustadt, P.C.

[57] ABSTRACT

Sebum is selectively removed from facial skin without removing make-up by spraying a liquid composition on to the skin and holding a water absorptive or oil absorptive material against the skin to remove the sebum together with the liquid composition.

6 Claims, No Drawings

SELECTIVE REMOVING METHOD OF SEBUM

BACKGROUND OF THE INVENTION

1. Field of the Invention

The present invention relates to a method for selectively removing sebum from the skin and also a method for adjusting makeup, each without removing makeup from the made-up face.

2. Description of the Related Art

Many women complain that excess secretion of sebum makes their face, particularly, forehead, nose or chin oily or sticky and ruins their makeup. As a sebum removing method, frequent face cleansing or use of sebum removing paper by holding it against the face is conventionally known. Although face cleansing has high sebum removing effects, it removes not only the sebum but also the foundation or lipstick without selectivity. Therefore the face needs re-makeup after cleansing, causing a problem of inconvenience. In addition, use of a cleansing agent having high detergency or frequent face washing tends to make the skin rough, taut or dry.

Sebum removing paper, on the other hand, can remove sebum selectively and easily without removing the makeup from the made-up face so that it has been popular as a usual makeup adjusting method. But, users have often expressed dissatisfaction with it, because owing to relatively low sebum removing effects, the face becomes oily soon after use or plural sheets of paper must be used each time.

An object of the present invention is therefore to provide a method for removing sebum selectively and effectively from the skin and also a makeup adjusting method, each without removing the makeup from the made-up face.

SUMMARY OF THE INVENTION

In one aspect of the present invention, there is thus provided a selective sebum removing method which comprises spraying a liquid composition to a made-up skin, holding a water absorptive or oil absorptive material against the skin, thereby removing the sebum together with the liquid composition.

In another aspect of the present invention, there is also provided a makeup adjusting method which comprises spraying a liquid composition to a made-up skin, holding a water absorptive or oil absorptive material against the skin, and then adjusting the makeup.

In a further aspect of the present invention, there are also provided a selective sebum removing mist and makeup adjustment pre-care mist each of which comprises a hydrophilic surfactant and/or ethanol and has an average particle size of 30 to 200 μm.

PREFERRED EMBODIMENTS OF THE INVENTION

There is no particular limitation imposed on the liquid composition to be used in the present invention insofar as it is in a liquid form and can be sprayed at room temperature. Any one of water, aqueous liquid compositions and oily liquid compositions can be used. Among them, aqueous liquid compositions are preferred because they impart the skin with dry and refreshed touch feelings after sebum removal.

It is preferred to incorporate a hydrophilic surfactant and/or ethanol in the aqueous liquid composition. Here, as the hydrophilic surfactant, any one of nonionic surfactants, anionic surfactants, amphoteric surfactants and cationic surfactants can be employed.

Specific examples of the nonionic surfactant include polyoxyethylene addition type surfactants such as polyoxyethylene castor oil or polyoxyethylene hydrogenated castor oil derivatives, polyoxyethylene sorbitan fatty acid esters, polyoxyethylene glycerin fatty acid esters, polyoxyethylene sorbitol fatty acid esters, polyoxyethylene alkyl ethers, polyoxyethylene alkyl phenyl ethers and polyoxyethylene polyoxypropylene block polymers; polyglycerin alkyl ethers, polyglycerin fatty acid esters, sucrose fatty acid esters and alkyl glucosides.

Examples of the anionic surfactants include N-acylamino acid salts such as sodium lauroyl sarcosinate and sodium lauroyl methyl alanine; polyoxyethylene alkylether phosphates, polyoxyethylene alkylsulfates, alkyl sulfates, alkylphosphates and fatty acid salts.

Examples of the amphoteric surfactant include alkylbetaines and alkylamidobetaines.

Examples of the cationic surfactant include di(long-chain alkyl) quaternary ammonium salts, mono(long-chain alkyl) quaternary ammonium salts, bis(hydroxyalkyl) quaternary ammonium salts, and amide/ester-group-containing quaternary ammonium salts.

Among them, preferred is that having a contact angle of 60° or less when measured 20 seconds after the dropwise addition of 1.2 μL of it in the form of a 0.5 wt. % aqueous solution onto a polyurethane-made artificial skin ("Bioskin No. F-901", trade name; product of Viewlux). In the present invention, the contact angle is a value as measured by a contact angle measuring meter (Kyowa Kaimen Kagakusha).

The hydrophilic surfactants can be used either singly or in combination. It is preferred to add the hydrophilic surfactant (s) to the liquid composition in a total amount of 0.001 to 5 wt. %, particularly 0.01 to 3 wt. %, because in such an amount, particularly good touch feeling of the skin can be attained after sebum removal.

Ethanol is preferably added in an amount of 0.01 to 20 wt. %, particularly 0.05 to 10 wt. % to the liquid composition from the viewpoints of enough sebum removing effects and low skin irritation.

When an oily liquid composition is used, on the other hand, examples of the oily component include hydrocarbon oils such as solid or liquid paraffin, vaseline and squalane; natural oils and fats such as eucalyptus oil, beef tallow, olive oil and jojoba oil; ester oils such as isopropyl myristate and neopentyl glycol dicaprate; higher fatty acids such as stearic acid and linoleic acid; higher alcohols such as cetanol and stearyl alcohol; phospholipids; naturally extracted sphingosine derivatives and synthesized products thereof; cholesterol derivatives such as cholesterol and cholesteryl isostearate; silicones such as methyl polysiloxane and methyl phenyl polysiloxane; cyclic silicones, modified silicones such as oxazoline modified silicone; and amide derivatives as described in Japanese Patent Applications Laid-Open Nos. Hei 8-319263 and Sho 62-228048.

In addition to the above-described component, components ordinarily employed for a cosmetic composition can be incorporated optionally in the liquid composition within an extent not damaging the advantages of the present invention. Examples include humectants, water-soluble polymers, acids, bases, salts, perfumes, colorants, antioxidants, ultraviolet absorbers, whitening agents, blood circulation promoters, vitamins, metal chelating agents, sebum controlling agents, powders, astringents, skin softeners, cool touch imparting agents, anti-inflammatory agents, proteins, amino acids, vegetable extracts.

A liquid composition having a contact angle of 80° or less, particularly 60° or less as measured in a similar manner to the above is preferred, because it fits well when sprayed to the skin.

In the present invention, first, such a liquid composition is sprayed to the skin. There is no particular limitation imposed on the spraying method of the liquid composition insofar as it can be sprayed to the skin in the form of a mist having an average particle size of 30 to 200 μm. For example, the liquid composition can be sprayed from a pump type spray container or a pressure container together with a propellant. As the container and propellant, those ordinarily employed for cosmetics can be used. Although there is no particular limitation on the amount to be sprayed, a range of 0.05 to 0.45 mL is preferred when sprayed to the whole face. In this manner, the liquid composition can be sprayed uniformly over the face and moreover, refreshed feeling can be attained.

In the next step, a water absorptive or oil absorptive material is held against the part to which the liquid composition has been sprayed. Examples of the water absorptive or oil absorptive material include a polymer gel, porous material and fibrous material. They can be used either singly or in combination.

Specific examples of the polymer gel include acrylic acid series water absorptive polymers. Those of the porous material include polymer materials such as polyamide and mineral materials such as silica, being used in the form of a sponge, sheet or puff. Specific examples of the fibrous material include pulp, hemp, cotton, rayon, acetate, acryl, polyester, polyethylene, polypropylene, polyurethane and polyamide. They can be used in a form of, for example, paper such as facial tissue, woven cloth, nonwoven cloth and facial cotton prepared by compression molding or in a mass form. By holding such a material against the skin, sebum can be removed selectively together with the sprayed liquid composition. The water absorptive material and oil absorptive material are used for the aqueous liquid composition and oily liquid composition, respectively.

When makeup is adjusted in an ordinary manner after the liquid composition of the present invention is sprayed to the made-up skin and the above-described material is held against thus-treated skin, good makeup spread and beautiful finish and moreover, the good makeup retention can be attained.

According to the present invention, sebum can be removed selectively by a simple method without removing the makeup from the made-up face. In addition, the method of the present invention brings about high sebum removing effects and therefore, makes it possible to remove stickiness or sebum-caused shining and impart the skin with dry tough feeling. Moreover, the spraying imparts the skin with refreshed feeling. When the makeup is adjusted, good makeup spread can be attained and makeup retention after adjustment is also good.

EXAMPLES

Example 1

Purified water was filled in a pump type spraying container and sprayed all over the face (spraying three times, sprayed amount: about 0.22 mL). Just after spraying, a facial tissue was held against the face. The mist had an average particle size of 80 μm.

Examples 2 to 7

In each of Examples 2 to 7, the liquid composition as shown in Table 1 was prepared in the conventional manner. The contact angle of the composition is also shown in Table 1. The composition was filled in a pump type spraying container and sprayed all over the face (spraying three times, sprayed amount: 0.22 mL). Just after the spraying, a facial tissue was held against the face. The mist had an average particle size of 86 μm.

TABLE 1

| Component (wt. %) | Ex. 2 Composition A | Ex. 3 Composition B | Ex. 4 Composition C | Ex. 5 Composition D | Ex. 6 Composition E | Ex. 7 Composition F |
|---|---|---|---|---|---|---|
| Diester of polyoxyethylene glyceryl glutamic acid and isostearic acid (25 EO)*1 | 0.8 | 0.8 | — | — | — | — |
| Polyoxyethylene hydrogenated castor oil (60 EO)*2 | — | — | 0.8 | — | — | — |
| Palmitic acid*3 | — | — | — | — | 0.45 | — |
| Stearic acid*4 | — | — | — | — | 0.55 | — |
| Potassium hydroxide | — | — | — | — | 0.27 | — |
| 95% ethanol | 5 | — | — | 5 | — | — |
| Menthol | 0.05 | 0.05 | 0.05 | 0.05 | 0.05 | — |
| Glycerin | 1 | 1 | 1 | 1 | 1 | — |
| Citric acid | 0.05 | 0.05 | 0.05 | 0.05 | 0.05 | — |
| Sodium citrate | 0.05 | 0.05 | 0.05 | 0.05 | 0.05 | — |
| Methyl paraoxybenzoate | 0.1 | 0.1 | 0.1 | 0.1 | 0.1 | — |
| Perfume | Trace | Trace | Trace | Trace | Trace | Trace |
| Squalane | — | — | — | — | — | 10.0 |
| Liquid isoparaffin | — | — | — | — | — | 29.0 |
| Methyl polysiloxane | — | — | — | — | — | 30.0 |
| Methyl cyclopolysiloxane | — | — | — | — | — | 30.0 |
| 99.8% ethanol | — | — | — | — | — | 1.0 |

TABLE 1-continued

| Component (wt. %) | Ex. 2 Composition A | Ex. 3 Composition B | Ex. 4 Composition C | Ex. 5 Composition D | Ex. 6 Composition E | Ex. 7 Composition F |
|---|---|---|---|---|---|---|
| Purified water | Balance | Balance | Balance | Balance | Balance | — |
| Contact angle of composition | 50° | 53° | 56° | 78° | 48° | <30° |

*[1]contact angle: 55°
*[2]contact angle: 62°
*[3]contact angle: 50° as potassium palmitate
*[4]contact angle: 52° as potassium stearate.

Example 8

A liquid composition similar to that used in Example 2 was filled in a pump type spraying container and sprayed all over the face (spraying three times, sprayed amount: about 0.22 mL). Just after spraying, a cotton handkerchief was held against the face. The mist had an average particle size of 90 μm.

Example 9

A liquid composition A similar to that used in Example 2 was filled in a pump type spraying container and sprayed all over the face (spraying three times, sprayed amount: about 0.22 mL). Just after spraying, facial cotton was held against the face. The mist had an average particle size of 90 μm.

Example 10

In an aerosol can, 75 parts of a liquid composition similar to that employed in Example 2 and 25 parts of a propellant (diethyl ether) were filled, followed by spraying all over the face (for about 5 seconds). Just after spraying, a facial tissue was held against the face. The mist had an average particle size of 92 μm.

Example 11

An aqueous liquid composition (G) as described below was prepared in a conventional manner. The composition had a contact angle of 35°.

The composition was filled in a pump type spraying container, followed by spraying all over the face (spraying three times, sprayed amount: about 0.22 mL). Just after spraying, a facial tissue was held against the face. The mist had an average particle size of 75 μm.

| (Components) | (wt. %) |
|---|---|
| Polyoxyethylene isocetyl ether (20 EO) (contact angle: 35°) | 1.2 |
| 1-Menthyl lactate | 0.05 |
| Urea | 0.05 |
| ε-Aminocaproic acid | 0.01 |
| 1,3-Butanediol | 1.0 |
| Polyethylene glycol 1500 | 2.0 |
| Succinic acid | 0.1 |
| Disodium phosphate | 0.2 |
| Benzoic acid | 0.3 |
| 95% Ethanol | 5.0 |
| Perfume | Trace |
| Purified water | Balance |

Example 12

An aqueous liquid composition (H) as described below was prepared in a conventional manner. The composition had a contact angle of 30°.

The composition was filled in a pump type spraying container, followed by spraying all over the face (spraying three times, sprayed amount: about 0.22 mL). Just after spraying, a facial tissue was held against the face. The mist had an average particle size of 55 μm.

| (Components) | (wt. %) |
|---|---|
| Polyethylene glycol monolaurate (contact angle: 40°) | 1.5 |
| 1-Menthyl glyceryl ether | 0.05 |
| Tris(ethoxyethoxyethyl)phosphate | 0.2 |
| Polyethylene glycol 1500 | 2.0 |
| Succinic acid | 0.1 |
| Disodium phosphate | 0.2 |
| Benzoic acid | 0.3 |
| Zinc p-phenolsulfonate | 0.05 |
| Perfume | Trace |
| Purified water | Balance |

Example 13

An aqueous liquid composition (I) as described below was prepared in a conventional manner. The composition had a contact angle of 35°.

The composition was filled in a pump type spraying container, followed by spraying all over the face (spraying three times, sprayed amount: about 0.22 mL). Just after spraying, a facial tissue was held against the face. The mist had an average particle size of 65 μm.

| (Components) | (wt. %) |
|---|---|
| Polyoxyethylene isocetyl ether (20 EO) (contact angle: 35°) | 1.0 |
| Neopentyl glycol dicaprate | 0.5 |
| Citric acid | 0.2 |
| Sodium citrate | 0.3 |
| 1,3-Propanediol | 1.2 |
| Glycerin | 1.0 |
| Methyl paraoxybenzoate | 0.2 |
| Purified water | Balance |

Comparative Example 1

After coating of a foundation, sebum removing behavior was not taken at all.

Comparative Example 2

The sebum was removed in a daily manner by using sebum removing paper.

Comparative Example 3

A liquid composition A similar to that used in Example 2 was filled in a pump type spraying container, followed by spraying all over the face (spraying three times, sprayed amount: 0.22 mL). The face was dried naturally without holding anything against the skin. The mist had an average particle size of 90 μm.

Comparative Example 4

A liquid composition A similar to that used in Example 2 was filled in a pump type spraying container, followed by spraying all over the face (spraying three times, sprayed amount: 0.22 mL). The face was wiped with a facial tissue. The mist had an average particle size of 90 μm.

Comparative Example 5

Facial cotton was impregnated with a liquid composition A similar to that employed in Example 2 in an amount 8 times the weight of the cotton and it was held against the face.

Test 1

With regards to the sebum removing operation carried out in Examples 1 to 13 and Comparative Examples 1 to 5, the sebum removing effect (remaining amount of sebum), selectivity to sebum, dry touch feeling just after operation, makeup spread and makeup retention were evaluated. The results are shown in Tables 2 and 3.

Evaluation methods (1) Sebum removing effect (remaining amount of sebum)

After face cleansing, foundation was applied to the face. Four hours after the makeup, which means the time when makeup fading starts to be recognized, one side of the forehead [designated as an untreated portion (Comparative Example 1)] was not subjected to any sebum removing operation while the other side was subjected to any one of the operations in Examples 1 to 13 and Comparative Examples 2 to 5. Rightly after the treatment, sebum in a predetermined area of each portion of the forehead was extracted with acetone/ether (50:50). The resulting solution was filtered, followed by concentration to dryness. The solid was then re-dissolved in hexane at a fixed dilution ratio. The resulting solution was subjected to gas chromatography, whereby an amount of squalene per 1 $cm^2$ of each portion of the forehead was determined.

The amount of squalene obtained by each operation (each of Examples 1 to 13 and Comparative Examples 2 to 5) was calculated with that of the untreated portion (Comparative Example 1) as 100 and it was designated as the remaining amount of sebum (%). The results are shown as an average value of 10 samples.

(2) Selectivity to sebum

Twenty women who had usually experienced makeup fading due to sebum were asked if the coming-off of the foundation after each of the sebum removing operations was uncomfortable or not and each operation was judged based on the following standards.

A: Two out of 20 women answered yes.

B: At least 3 but not greater than 5 out of 20 women answered yes.

C: At least 6 out of 20 women answered yes.

(3) Dry touch feeling rightly after operation, makeup spread upon adjustment of makeup and makeup retention after adjustment.

Twenty women who had usually experienced makeup fading due to sebum and therefore used sebum removing paper were asked to evaluate, as touch feeling of the skin after removal of sebum by each of the sebum removing operations, dry touch feeling rightly after operation, makeup spread upon adjustment of makeup and makeup retention after adjustment in comparison with the daily operation. They were judged based on the following standards:

A: Out of 20 women, 16 answered good.

B: Out of 20 women, at least 12 but less than 16 answered good.

C: Out of 20 women, at least 8 not less than 12 answered good.

D: Out of 20 women, not less than 8 answered good.

TABLE 2

| | Examples | | | | | | | | | | |
|---|---|---|---|---|---|---|---|---|---|---|---|
| | 1 | 2 | 3 | 4 | 5 | 6 | 7 | 8 | 9 | 10 | 11 |
| Liquid composition to be employed | Purified water | A | B | C | D | E | F | A | A | A | G |
| Applying (spraying) method | Pump type spraying container | Pump type spraying container | Pump type spraying container | Pump type spraying container | Pump type spraying container | Pump type spraying container | Pump type spraying container | Pump type spraying container | Pump type spraying container | Aerosol | Pump type spraying container |
| Material to be held against the skin | Facial tissue | Facial tissue | Facial tissue | Facial tissue | Facial tissue | Facial tissue | Facial tissue | Handkerchief (cotton) | Facial cotton | Facial tissue | Facial tissue |
| Remaining amount of sebum (%) | 51 | 36 | 38 | 45 | 39 | 39 | 55 | 40 | 42 | 36 | 34 |
| Selectivity to sebum | B | B | B | B | B | B | B | B | B | B | B |
| Dry touch feeling rightly after application | B | A | A | B | A | A | B | A | A | A | A |
| Makeup spread | B | A | A | A | A | A | B | A | A | A | A |
| Makeup retention | B | A | A | B | A | A | B | A | A | A | A |

TABLE 3

|  | Examples | | Comparative Examples | | | | |
|---|---|---|---|---|---|---|---|
| Liquid composition to be employed | 12<br>H | 13<br>I | 1<br>— | 2<br>— | 3<br>A | 4<br>A | 5<br>A |
| Applying (spraying) method | Pump type spraying container | Pump type spraying container | — | — | Pump type spraying container | Pump type spraying container | Cotton impregnated with A in advance is held against the skin |
| Material to be held against the skin | Facial tissue | Facial tissue | — | Sebum removing paper | — | Rubbing with Facial tissue | |
| Remaining amount of sebum (%) | 35 | 40 | 100 | 63 | 102 | 40 | 83 |
| Selectivity to sebum | B | B | B | B | B | D | B |
| Dry touch feeling rightly after application | A | A | D | C | D | A | D |
| Makeup spread | A | A | D | C | C | A | D |
| Makeup retention | A | A | D | C | C | A | D |

Japanese Patent Application Nos. 10-041869 and 10-245646, filed on Feb. 24, 1998 and Aug. 31, 1998, respectively, are incorporated herein by reference.

What is claimed is:

1. A method of selectively removing sebum from the skin, which comprises:

spraying a liquid composition to the skin, and holding a water absorptive or oil absorptive material against the skin, thereby removing sebum together with the liquid composition, wherein the liquid composition comprises:
 a) 0.001% to 5% by weight of a hydrophilic surfactant selected from the group consisting of nonionic, anionic, amphoteric and cationic hydrophilic surfactants, or
 b) an oily component selected from the group consisting of a hydrocarbon oil, a natural oil, a fat, an ester oil, a higher fatty acid, a phospholipid, naturally extracted sphingosine derivative and synthesized products thereof, cholesterol and derivatives thereof, silicones, modified silicone and an amide derivative; and wherein the water absorptive or oil absorptive material is selected from the group consisting of a polymer gel, a porous material and a fibrous material.

2. The method of selectively removing sebum according to claim 1, wherein the liquid composition is an aqueous liquid composition and the water absorptive material is held against the skin.

3. A method of adjusting make-up, which comprises:

spraying a liquid composition to made-up skin, holding a water absorptive or oil absorptive material against the skin, and adjusting the make-up, wherein the liquid composition comprises:
 a) 0.001% to 5% by weight of a hydrophilic surfactant selected from the group consisting of nonionic, anionic, amphoteric and cationic hydrophilic surfactants, or
 b) an oily component selected from the group consisting of a hydrocarbon oil, a natural oil, a fat, an ester oil, a higher fatty acid, a phospholipid, naturally extracted sphingosine derivative and synthesized products thereof, cholesterol and derivatives thereof, silicones, modified silicone and an amide derivative; and wherein the water absorptive or oil absorptive material is selected from the group consisting of a polymer gel, a porous material and a fibrous material.

4. The method of adjusting makeup of claim 3, wherein the liquid composition has a contact angle of 80° or less when measured 20 seconds after the dropwise addition of the composition in an amount of 1.2 $\mu$L to a polyurethane-made artificial skin.

5. The method of claim 1, wherein the skin has make-up thereon.

6. A method of selectively removing sebum from the skin, which comprises:

spraying the liquid composition of claim 1 as a mist of particles having an average size of 30–200 $\mu$m onto the skin; and holding a water absorptive or oil absorptive material against the skin, thereby removing sebum together with the liquid composition.

* * * * *